(12) United States Patent
Sicken et al.

(10) Patent No.: US 6,600,067 B2
(45) Date of Patent: Jul. 29, 2003

(54) PROCESS FOR PREPARING ETHYLENEDIPHOSPHONIC ACIDS

(75) Inventors: Martin Sicken, Köln (DE); Hans-Peter Schmitz, Brühl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/025,712

(22) Filed: Dec. 19, 2001

(65) Prior Publication Data

US 2002/0082447 A1 Jun. 27, 2002

(30) Foreign Application Priority Data

Dec. 23, 2000 (DE) ......................................... 100 65 053

(51) Int. Cl.$^7$ ................................................. C07F 9/38
(52) U.S. Cl. ......................................................... 562/20
(58) Field of Search ......................................... 562/8, 20

(56) References Cited

U.S. PATENT DOCUMENTS 2,957,931 A * 10/1960 Hamilton et al. ............. 554/78
5,783,728 A * 7/1998 Kneller et al. ................ 562/21
6,420,598 B1 * 7/2002 Weferling et al. ............. 562/8

* cited by examiner

Primary Examiner—Jean F. Vollano
(74) Attorney, Agent, or Firm—Anthony A. Bisulca

(57) ABSTRACT

The invention relates to a process for preparing ethylenediphosphonic acids of the formula I,

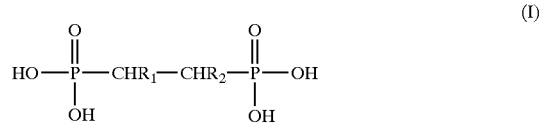

(I)

where $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatic systems, which comprises reacting phosphorous acid ($H_3PO_3$) directly with alkynes.

21 Claims, No Drawings

PROCESS FOR PREPARING ETHYLENEDIPHOSPHONIC ACIDS

BACKGROUND OF THE INVENTION

The present invention relates to a process for preparing ethylenediphosphonic acids of the formula I,

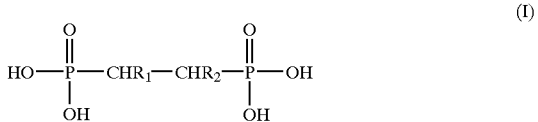

where $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatic systems.

Phosphonic acids are of great industrial importance, and the acids or their salts and esters are widely used in a very extensive variety of application sectors. Examples of applications of phosphonic acids are water softening, ore floatation, heavy metal complexing, and their use as starting materials for preparing flame retardants, pharmaceutical products, and pesticides.

The many types of application using phosphonic acids to form salts or complexes mainly use di- and polyphosphonic acids. Ethylenediphosphonic acids of the formula (I)

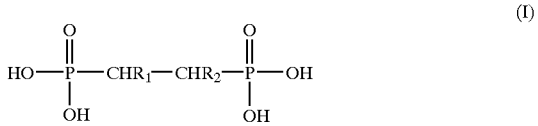

are particularly important here.

The known prior art uses complicated multistage syntheses to prepare ethylenediphosphonic acid (where $R_1$ and $R_2$ in formula I are hydrogen).

For example, K. Moedritzer, R. R. Irani, J. Inorg. Nucl. Chem. 22 (1961) 297–304 describes by way of example a process which begins by reacting diethyl β-chloroethylphosphonate with potassium diethyl phosphonate to give tetraethyl ethylenediphosponate, which is then converted into the desired ethylenediphosphonic acid by hydrolysis with concentrated hydrochloric acid.

DE 21 58 765 A1 proposes a process which begins by reacting triphenyl phosphite with tris(chloroethyl)phosphite with elimination of dichloroethane to give tetraphenyl ethylenediphosphonate, which is then converted into the desired ethylenediphosphonic acid under acidic or alkaline conditions, with cleavage of phenol.

The process described in S. M. Shner, L. P. Bocharova, I. K. Rubtsova, J. Gen. Chem. USSR 37 (1967 390–392) also starts from tris(chloroethyl) phosphite, which is reacted with ethyne(acetylene) to give tetrakis(chloroethyl) ethylenediphosphonate, which is then converted into the desired ethylenediphosphonic acid by hydrolysis under acidic conditions.

Disadvantages common to all of the above processes are that the starting materials themselves require complicated and expensive preparation, the yields obtained are inadequate, and considerable amounts of undesirable byproducts are produced, for example alkyl halides and phenols. This makes the processes uneconomic and environmentally unsatisfactory, so that ethylenediphosphonic acids prepared by these processes are almost impossible to obtain and therefore are not available for use in many possible applications.

There is therefore a requirement for a process which prepares ethylenediphosphonic acids and is simple to carry out, and gives a high yield of pure products. This process should also be markedly superior in economic and environmental terms to those previously known, by using readily obtainable or readily synthesizable starting materials and producing no undesirable byproducts.

SUMMARY OF THE INVENTION

The object on which the invention is based is therefore to provide a process whch prepares ethylenediphosphonic acids and avoids the abovementioned disadvantages, and gives the desired product in a single stage, starting from simple and readily obtainable materials.

This object is achieved by way of a process of the type mentioned at the outset, which comprises reacting phosphorous acid ($H_3PO_3$) directly with alkynes.

DETAILED DESCRIPTION OF THE INVENTION

The process of the invention has high selectivity and gives the corresponding ethylenediphosphonic acids in very good yields. This is particularly surprising since the experiments described in C. E. Griffin, H. J. Wells, J. Org. Chem. 24 (1959) 2049 give only low yields and considerable extent of side reactions on reacting phosphorous acid with olefins.

Compared with the processes previously known, the process of the invention has considerable advantages since it is single-stage, requires no use of complicated or halogen-containing starting materials, produces hardly any byproducts, and is overall an extremely economic process.

The phosphorous acid is preferably reacted with alkynes in the presence of a free-radical initiator.

The free-radical initiators used preferably comprise azo compounds.

The azo compounds are preferably cationic and/or non-cationic azo compounds.

The cationic azo compounds used preferably comprise 2,2'-azobis(2-amidinopropane) dihydrochloride or 2,2'-azobis(N,N'-dimethyleneisobutyramidine) dihydrochloride.

The noncationic azo compounds used preferably comprise azobis(isobutyronitrile), 4,4'-azobis(4-cyanopentanoic acid), or 2,2'-azobis (2-methylbutyronitrile).

The free-radical initiators used preferably comprise peroxidic inorganic and/or peroxidic organic free-radical initiators.

The peroxidic inorganic free-radical initiators used preferably comprise hydrogen peroxide, ammonium peroxodisulfate, and/or potassium peroxodisulfate.

The peroxidic organic free-radical initiators used preferably comprise dibenzoyl peroxide, di-tert-butyl peroxide, and/or peracetic acid.

A wide selection of suitable free-radical initiators can be found by way of example in Houben-Weyl, Supplementary volume 20, in the chapter "Polymerisation durch radikalische Initiierung" [Free-radical-initiated polymerization] on pages 15–74.

The free-radical initiators are preferably metered in continuously during the reaction.

The free-radical initiators metered in continuously during the reaction are preferably in the form of a solution in the alkyne.

The free-radical initiators metered in continuously during the reaction are preferably in the form of a solution in the solvent used.

To prepare the ethylenediphosphonic acids, phosphorous acid is reacted in the presence of a free-radical initiator with alkynes of the formula (II)

(II)

where $R_1$ and $R_2$ are identical or different and are hydrogen, a carboxy group, a carboxylic acid derivative, an unsubstituted or substituted alkyl group having from 1 to 10 carbon atoms, phenyl, benzyl, or alkyl-substituted aromatic systems.

The alkynes used may be either the unsubstituted ethyne (acetylene) where $R_1$ and $R_2$=H in formula (II), singly substituted derivatives where $R_1$=H and $R_2 \neq H$ in formula (II), or else doubly substituted alkynes where $R_1$ and $R_2 \neq H$ in formula (II).

Examples of these alkynes are ethyne(acetylene), phenylacetylene, diphenylacetylene, propyne, 1-butyne, 2-butyne, 1-phenylbutyne, 1-pentyne, 2-pentyne, 1-phenyl-1-pentyne, 1-hexyne, 2-hexyne, 3-hexyne, 1-phenyl-1-hexyne, 1-heptyne, 1-octyne, 4-octyne, 1-nonyne, 1-decyne, 1-dodecyne, the alkynols propargyl alcohol, 1-butyn-3-ol, 2-butyn-1-ol, 2-butyne-1,4-diol, 1-pentyn-3-ol, 2-pentyn-1-ol, 4-pentyn-1-ol, 4-pentyn-2-ol, 3-hexyn-1-ol, 5-hexyn-1-ol, 3-hexyne-2,5-diol, 2-octyn-1-ol, 1-octyn-3-ol, 3-nonyn-1-ol, 3-decyn-1-ol, and also propargyl chloride, propargyl bromide, propargylamine, propiolic acid, methyl propiolate, ethyl propiolate, 2-butynoic acid, ethyl 2-butynoate, 4-pentynoic acid, 5-hexynonitrile, 2-octynoic acid, methyl 2-octynoate, methyl 2-nonynoate, acetylenedicarboxylic acid, diethyl acetylenedicarboxylate, and dimethyl acetylenedicarboxylate.

Preferred alkynes are the 1-alkynes, propargyl alcohol, butynediol, propiolic acid and derivatives of acetylenedicarboxylic acid.

Particular preference is given to the use of ethyne (acetylene).

The reaction preferably takes place at a temperature of from 40 to 200 °C.

The reaction particularly preferably takes place at a temperature of from 70 to 130° C.

The reaction preferably takes place without a solvent in the $H_3PO_3$ melt.

The reaction preferably takes place in the presence of a solvent.

The solvent in which the reaction takes place is preferably acetic acid or water.

The reaction preferably takes place by introducing gaseous ethyne (acetylene) at atmospheric pressure.

The reaction preferably takes place at superatmospheric pressure.

The manner of conducting the process is preferably such that after partial conversion the precipitating ethylenediphosphonic acid is filtered off, and further ethyne (acetylene) is added after replacing the phosphorous acid consumed.

The present invention in particular also provides a process in which phosphorous acid is reacted with ethyne(acetylene) in the presence of a cationic or noncationic free-radical initiator, or in the presence of a peroxidic free-radical initiator, to give ethylenediphosphonic acid.

The present invention in particular also encompasses a process in which phosphorous acid is reacted with ethyne (acetylene) in the presence of a cationic or noncationic free-radical initiator, or in the presence of a peroxidic free-radical initiator, to give ethylenediphosphonic acid, and this is removed continuously from the reaction mixture by a circulating filter system, and the phosphorous acid consumed is likewise replaced continuously by fresh acid.

The desired ethylenediphosphonic acids are obtained with high selectivity and high purity.

Either the phosphorous acid or else the alkynes may be used in excess, since the reaction partners always react in a molar ratio of 2 to 1 (phosphorous acid to alkyne).

EXAMPLES

The examples below illustrate the invention:

Example 1

Ethylenediphosphonic Acid

Gaseous ethyne(acetylene) was passed for a period of 10 h at a temperature of about 100° C. into 164 g (2 mol) of molten phosphorous acid in a heatable glass tubular reactor with gas-feed frit. At the same time, a solution of 23 g (0.1 mol) of ammonium peroxodisulfate in 50 g of water was metered in uniformly over the same period. After a continued reaction time of 0.5 h, removal of the ethyne(acetylene) by passing nitrogen through the mixture, and cooling to room temperature, the reaction mixture was freed from the water which had been introduced, filtered, washed twice, on each occasion using 200 ml of water, and dried at 130° C. under the suction provided by a water jet. This gave 82 g of a white crystalline solid with a melting point of 211° C., corresponding to a yield of 77.4%, based on the phosphorous acid used. Elemental analysis confirms the proposed structure: P: calc. 33.7%/found 31.6%; C.: calc. 26.1%/found 26.7%; H: calc. 5.4%/found 5.7%; $^{31}$P NMR spectrum (NaOD): δ=30 ppm (singlet); Purity ($^{31}$P NMR): 99%.

Example 2

Ethylenediphosphonic Acid

Gaseous ethyne(acetylene) was passed for a period of 10 h at a temperature of about 100° C. into 164 g (2 mol) of molten phosphorous acid in a heatable glass tubular reactor with gas-feed frit. At the same time, a solution of 23 g (0.1 mol) of ammonium peroxodisulfate in 50 g of water, and also 107 g of molten phosphorous acid, were metered in uniformly over the same period. During the reaction, the reaction mixture was continuously freed from precipitating ethylenediphosphonic acid by way of a frit and equipment for pumped circulation. The filter cake was washed twice, on each occasion with 200 ml of water, and dried at 130° C. under the suction provided by a water jet. This gave 69 g of ethylenediphosphonic acid at 99% purity ($^{31}$P NMR), corresponding to a yield of 65%, based on the amount of phosphorous acid starting material used. Ethyne(acetylene) was then passed into the reaction mixture under the same conditions, whereupon more ethylenediphosphonic acid precipitated.

What is claimed is:
1. A process for preparing ethylenediphosphonic acids of the formula I,

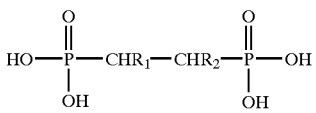 (I)

where $R_1$ and $R_2$ may be identical or different and are hydrogen, a carboxy group, an ester, an alcohol, an unsubstituted or substituted alkyl group having from 1 to 10 carbon atoms, phenyl, benzyl, alkyl-substituted aromatic systems, which comprises reacting phosphorous acid ($H_3PO_3$) directly with alkynes, wherein the reaction takes place without solvent in the $H_3PO_3$ melt.

2. The process as claimed in claim 1, wherein the phosphorous acid is reacted with alkynes in the presence of a free-radical initiator.

3. The process as claimed in claim 2, wherein the free-radical initiator used comprises azo compounds.

4. The process as claimed in claim 3, wherein the azo compounds comprise cationic and/or noncationic azo compounds.

5. The process as claimed in claim 4, wherein the cationic azo compounds are selected from the group consisting of 2,2'-azobis(2-amidinopropane) dihydrochloride and 2,2'-azobis(N,N'-dimethyleneisobutyramidine) dihydrochloride.

6. The process as claimed in claim 4, wherein the noncationic azo compounds are selected from the group consisting of azobis(isobutyronitrile), 4,4'-azobis(4-cyanopentanoic acid), and 2,2'-azobis(2-methylbutyronitrile).

7. The process as claimed in claim 2, wherein the free-radical initiators are selected from the group consisting of peroxidic inorganic and peroxidic organic free-radical initiators.

8. The process as claimed in claim 7, wherein the peroxidic inorganic free-radical initiators are selected from the group consisting of hydrogen peroxide, ammonium peroxodisulfate, and potassium peroxodisulfate.

9. The process as claimed in claim 7, wherein the peroxidic organic free-radical initiators are selected from the group consisting of dibenzoyl peroxide, di-tert-butyl peroxide, and peracetic acid.

10. The process as claimed in claim 2, wherein the free-radical initiators are metered in continuously during the reaction.

11. The process as claimed in claim 10, wherein the free-radical initiators metered in continuously during the reaction are in the form of a solution in the alkyne.

12. The process as claimed in claim 1, wherein the alkynes have the formula II

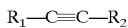 (II)

where $R_1$ and $R_2$ are identical or different and are hydrogen, a carboxy group, an ester, an alcohol, an unsubstituted or substituted alkyl group having from 1 to 10 carbon atoms, phenyl, benzyl, or alkyl-substituted aromatic systems.

13. The process as claimed in claim 1, wherein the alkynes are selected from the group consisting of ethyne (acetylene), phenylacetylene, diphenylacetylene, propyne, 1-butyne, 2-butyne, 1-phenylbutyne, 1-pentyne 2-pentyne, 1-phenyl-1-pentyne, 1-hexyne, 2-hexyne, 3-hexyne, 1-phenyl-1-hexyn, 1-heptyne, 1-octyne, 4-octyne, 1-nonyne, 1-decyne, 1-dodecyne, the alkynols propargyl alcohol, 1-butyn-3-ol, 2-butyn-1-ol, 2-butyne-1,4-diol, 1-pentyn-3-ol, 2-pentyn-1-ol, 4-pentyn-1-ol, 4-pentyn-2-ol, 3-hexyn-1-ol, 5-hexyn-1-ol, 3-hexyne-2,5-diol, 2-octyn-1-ol, 1-octyn-3-ol, 3-nonyn-1-ol, 3-decyn-1-ol, propargyl chloride, propargyl bromide, propargylamine, propiolic acid, methyl propiolate, ethyl propiolate, 2-butynoic acid, ethyl 2-butynoate, 4-pentynoic acid, 5-hexynonitrile, 2-octynoic acid, methyl 2-octynoate, methyl 2-nonynoate, acetylenedicarboxylic acid, diethyl acetylenedicarboxylate, and dimethyl acetylenedicarboxylate.

14. The process as claimed in claim 1, wherein the alkynes used are 1-alkynes, propargyl alcohol, butynediol, propiolic acid, diethyl acetylenedicarboxylate or dimethyl acetylenedicarboxylate.

15. The process as claimed in claim 1, wherein the alkyne is ethyne (acetylene).

16. The process as claimed in claim 1, wherein the reaction takes place at a temperature of from 40 to 200° C.

17. The process as claimed in claim 1, wherein the reaction takes place at a temperature of from 70 to 130° C.

18. The process as claimed in claim 1, wherein the reaction takes place by introducing gaseous ethyne (acetylene) at atmospheric pressure.

19. The process as claimed in claim 1, wherein the reaction takes place at superatmospheric pressure.

20. The process as claimed in claim 1, wherein phosphorous acid is reacted with ethyne(acetylene) in the presence of a cationic or noncationic free-radical initiator, or in the presence of a peroxidic free-radical initiator, to give ethylenediphosphonic acid.

21. The process as claimed in claim 1, wherein phosphorous acid is reacted with ethyne(acetylene) in the presence of a cationic or noncationic free-radical initiator, or in the presence of a peroxidic free-radical initiator, to give ethylenediphosphonic acid, and this is removed continuously from the reaction mixture by a circulating filter system, and the phosphorous acid consumed is likewise replaced continuously by fresh acid.

* * * * *